United States Patent [19]
Shinn et al.

[11] Patent Number: 5,683,465
[45] Date of Patent: Nov. 4, 1997

[54] ARTIFICIAL INTERVERTEBRAL DISK PROSTHESIS

[76] Inventors: Gary Lee Shinn, 1543 Bleistein, Cody, Wyo. 82414; James Daryl Tate, 2900 Eureka Way, Redding, Calif. 96001

[21] Appl. No.: 617,217

[22] Filed: Mar. 18, 1996

[51] Int. Cl.$^6$ .................................................. A61F 2/44
[52] U.S. Cl. .................................................. 623/17
[58] Field of Search ............................ 623/17; 606/61

[56] References Cited

U.S. PATENT DOCUMENTS

| | | | |
|---|---|---|---|
| 4,759,769 | 7/1988 | Hedman et al. | 623/17 |
| 4,770,659 | 9/1988 | Kendall | 623/22 |
| 4,919,666 | 4/1990 | Buchhorn et al. | 623/16 |
| 5,047,055 | 9/1991 | Bao et al. | 623/17 |
| 5,192,326 | 3/1993 | Bao et al. | 623/17 |
| 5,246,458 | 9/1993 | Graham | 623/17 |
| 5,314,477 | 5/1994 | Marnay | 623/17 |
| 5,458,642 | 10/1995 | Beer et al. | 623/17 |
| 5,507,816 | 4/1996 | Bullivant | 623/17 |

*Primary Examiner*—David Isabella
*Assistant Examiner*—John M. Black
*Attorney, Agent, or Firm*—Risto A. Rinne, Jr.

[57] ABSTRACT

A prosthesis for the replacement of a spinal disk includes a first disk half and a second disk half. The first disk half includes a portion of a socket attached to a first plate. The second disk half includes a portion of a ball attached to a second plate. The socket includes a plurality of expansion slots which expand to allow the portion of a ball to be inserted into the socket and which then contract to retain the portion of a ball therein. A first hole is provided through the first plate, a second hole is provided through the socket, and a third hole is provided through the second plate which together form an opening through the disk. The opening is adapted to receive an insert to either medicate a pair of vertebrae or provide a barrier therein. The disk is fastened to the vertebrae by any preferred combination of pins, tabs, or a first annulus or second annulus, each of which extend from the disk. The tabs or the first annulus or the second annulus includes a hole therein that is adapted to receive a screw. A flexible substantially toroidal enclosure is attached to the perimeter of the first plate and to the perimeter of the second plate when desired to form a barrier between the disk and any proximal organic material.

24 Claims, 3 Drawing Sheets

ARTIFICIAL INTERVERTEBRAL DISK PROSTHESIS

BACKGROUND OF THE INVENTION

1. Field of the Invention

The present invention, in general, relates to surgical implant devices and, more particularly, to artificial intervertebral disk prostheses.

Intervertebral disk prostheses are generally known types of devices. However known types of intervertebral disk prostheses fail to provide, in combination, many of the attributes of the normal spinal disk that they are intended to replace.

For example, the ideal intervertebral disk prosthesis would possess a narrow depth, having a thickness similar to a normal (healthy) spinal disk so that the two vertebrae that it is placed between are disposed a normal distance apart from each other.

Also, an ideal intervertebral disk prosthesis would provide for tilt to occur in any direction.

Further, it would limit the maximum amount of tilt that is permitted to occur in any direction.

Yet even further, an ideal intervertebral disk prosthesis would allow for rotation about a central longitudinal axis to occur.

And still further, it would include anchoring means that resist dislodging of the prosthesis in the event of an impact applied to the rear of the user.

And still yet further, an ideal intervertebral disk prosthesis would provide an inherent retention of the various component parts thereof which tend to resist separation of the intervertebral disc during extension.

Even still yet further, an ideal intervertebral disk prosthesis would provide a hole through the prosthesis.

Certain of these desirable attributes are provided by some of the known prosthetic disk devices, and in particular by some of those types of devices which incorporate a ball and a socket type of arrangement. However these known prior types of devices fail to provide many of these attributes simultaneously in a intervertebral disk prosthesis which also possesses a narrow profile (thickness) and includes a hole through the prosthesis.

Accordingly there exists today a need for an Artificial Intervertebral Disk Prosthesis that incorporates simultaneously many of the above desirable features in a prosthesis that is approximately the same thickness as is the spinal disk it is intended to replace.

2. Description of Prior Art

Intervertebral prostheses are, in general, known. For example, the following patents describe various types of these devices:

U.S. Pat. No. 4,309,777 to Patil, Jan. 17, 1982;

U.S. Pat. No. 4,759,766 to Buettner-Janz et al, Jul. 26, 1988;

U.S. Pat. No. 4,863,477 to Monson, Sept. 5, 1988;

U.S. Pat. No. 4,946,378 to Hirayama et al, Aug. 7, 1990;

U.S. Pat. No. 4,997,432 to Keller, Mar. 5, 1991;

U.S. Pat. No. 5,071,437 to Steffee, Dec. 10, 1991;

U.S. Pat. No. 5,123,926 to Pisharodi, Jun. 23, 1992;

U.S. Pat. No. 5,171,281 to Parsons et al, Dec. 15, 1992;

U.S. Pat. No. 5,236,460 to Barber, Aug. 17, 1993;

U.S. Pat. No. 5,258,031 to Salib et al, Nov. 2, 1993;

U.S. Pat. No. 5,306,308 to Gross et al, Apr. 26, 1994;

U.S. Pat. No. 5,314,477 to Marnay, May 24, 1994;

U.S. Pat. No. 5,320,644 to Baumgartner, Jun. 14, 1994; and

U.S. Pat. No. 5,360,430 to Lin, Nov. 1, 1994.

The following foreign patents also describe various types of these devices:

United Kingdom EP 538183-A1 to Sulz; and

United Kingdom EP 60141-A1 to Lins.

While the structural arrangements of the above described devices, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an important object of the present invention to provide an artificial intervertebral disk prosthesis that is thin.

It is also an object of the invention to provide an artificial intervertebral disk prosthesis that allows for tilt to occur in any direction.

Another object of the invention is to provide an artificial intervertebral disk prosthesis that limits the amount of tilt that can occur in any direction.

Still another object of the invention is to provide an artificial intervertebral disk prosthesis that allows for rotation about a central longitudinal axis to occur.

Yet another object of the invention is to provide an artificial intervertebral disk prosthesis that resists dislodging of the prosthesis in the event of an impact to the user.

Still yet another object of the invention is to provide an artificial intervertebral disk prosthesis that includes structure adapted to retain the various component parts thereof in a position of cooperation with respect to each other when a force tending to extend the prosthesis occurs.

Still yet another important object of the invention is to provide an artificial intervertebral disk prosthesis that is easy to manufacture.

Still yet another very important object of the invention is to provide an artificial intervertebral disk prosthesis that is easy to assemble subsequent to the manufacture of the component parts thereof.

Still yet another further important object of the invention is to provide an artificial intervertebral disk prosthesis that contains a minimum number of component parts.

Another important object of the invention is to provide an artificial intervertebral disk prosthesis that provides an opening intermediate two adjacent vertebrae.

Still yet another further very important object of the invention is to provide an artificial intervertebral disk prosthesis that is adapted to receive at least one insert therein.

Briefly, an artificial intervertebral disk prosthesis that is constructed in accordance with the principles of the present invention has a first disk half and a second disk half. The first disk half includes a first plate having a "D-shaped" profile and includes a portion of a socket attached thereto and includes a first hole through the first plate and within the socket. The socket is adapted to permit expansion of a portion thereof to receive a portion of a ball that is attached to a second plate of the second disk half. The second plate has a "D-shaped" profile similar to that of the first plate and includes a second hole through the socket and a third hole through the second plate that is adjacent to the second hole. The first hole, the second hole, and the third hole form a contiguous opening that passes through the disk. The ball is sized so as to cooperate with the socket and resist extension apart from the socket once inserted therein. The disk prosthesis is retained in position by the use of either tabs attached to the first plate or to the second plate or both, or by the use of a first annulus attached to the first plate, or by a second annulus attached to the second plate, or by both the first annulus and the second annulus, or by a plurality of first pins which protrude from the first plate side opposite to the side having the socket attached or by a plurality of second pins which protrude from the second plate side opposite to the side having the ball attached or by both the first pins and the second pins, or by any desired combination of any of the above described tabs, annulus', or pins. An optional flexible toroidal enclosure is described which provides a barrier intermediate the disk prosthesis and its surroundings that is useful to prevent scar tissue from forming inside of the artificial disk prosthesis as well as to prevent any proximal organic matter from entering into the prosthesis.

DETAILED DESCRIPTION OF THE INVENTION

Figure 1:
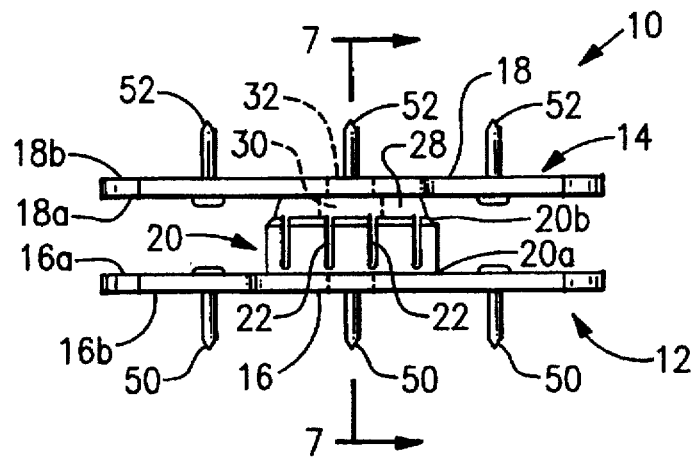
FIG. 1 is a side view of an artificial intervertebral disk prosthesis disposed in a level attitude.

Referring on occasion to all of FIGURE drawings and now in particular to FIGS. 1, 2, 7 and 8 is shown, an artificial intervertebral disk prosthesis, identified in general by the reference numeral 10.

The disk 10 includes a first disk half 12 and a second disk half 14 which together, form the two main component assembly parts of the disk 10.

The first disk half 12 includes a first plate 16 which has, in general, a "D-shaped" profile and a first side 16a thereof and a second side 16b thereof. The second disk half 14 includes a second plate 18 which also has, in general, a "D-shaped" profile and a first side 18a thereof and a second side 18b thereof. The "D-shaped" profile of the first disk half 12 and of the second disk half 14 are well known preferred attributes of spinal disk prostheses as this shape approximates the cross sectional profile of a vertebra (not shown).

Figure 8:
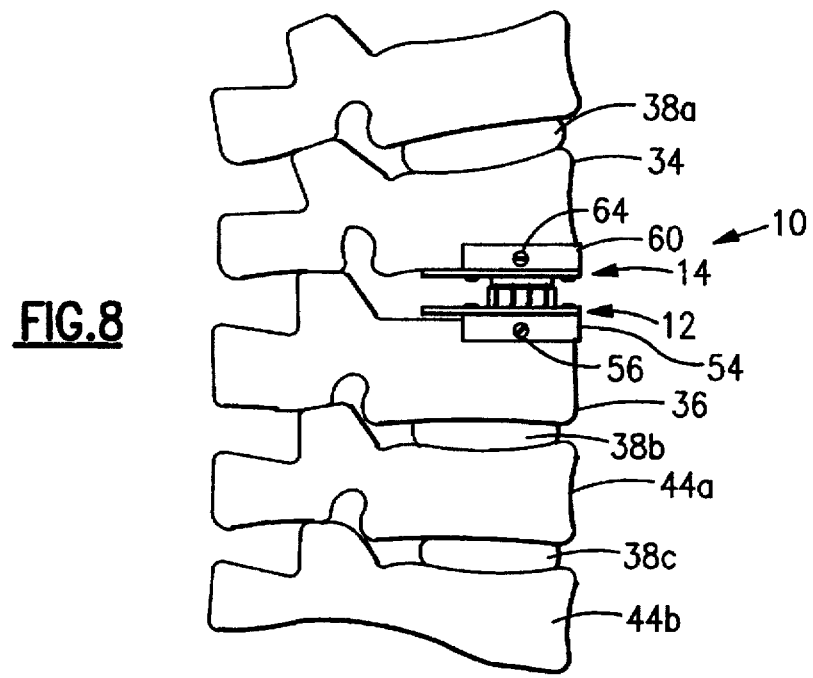
FIG. 8 is a side view of the disk disposed intermediate a pair of adjacent vertebrae.

Both the first plate 16 and the second plate 18 are approximately the same size so as to adapt to the size of two adjacent vertebrae (See FIG. 8). Of course the size of the first plate 16 and the size of the second plate 18 and all of other component parts of the disk 10 as are described hereinbelow are varied in size to correspond with the size of any of two adjacent vertebrae that are found in an entire spinal column (not shown).

Similarly the material used to construct either the first disk half 12 or the second disk half 14 is selected to prevent rejection from occurring whilst still preserving the proper functioning of the disk 10. Although various metals such as titanium, aluminum, and steel each have desirable properties, the preferred selection of material to be used for the construction of the disk 10 shall be determined by trials upon animals (not shown) and eventually human trials and by laboratory testing. Plastics and composite materials may similarly be used and, of course, the various component parts of the disk 10 as described herein may each be formed of dissimilar materials if preferred.

A socket, identified in general by the reference numeral 20, is attached to the first side 16a of the first plate 16 at a first socket end 20a. The socket 20 extends up from the first plate 16 a predetermined distance and encompasses a circular area about the first plate terminating at a second socket end 20b.

A series of expansion slots 22 are provided in the socket 20 beginning at the second socket end 20b and extending a predetermined distance toward the first socket end 20a. The purpose of the expansion slots 22 is to allow the socket 20 to expand during assembly of the disk 10 when the second disk half 14 is attached to the first disk half 12, as is described in greater detail hereinbelow.

Figure 2:
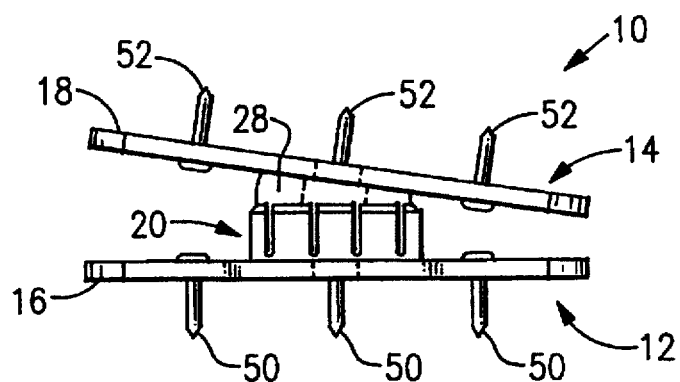
FIG. 2 is a side view of an artificial intervertebral disk prosthesis disposed in an angled (tilted) attitude.
Figure 3:
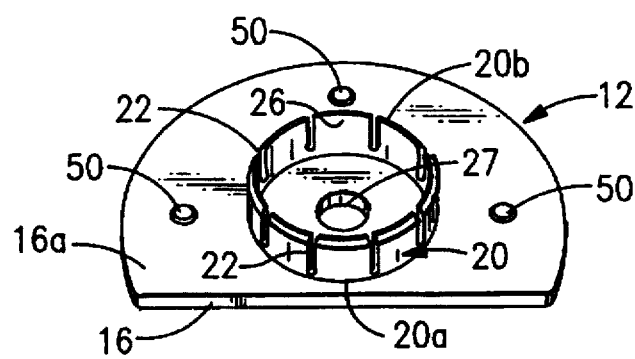
FIG. 3 is a view in perspective of a first disk half.
Figure 7:
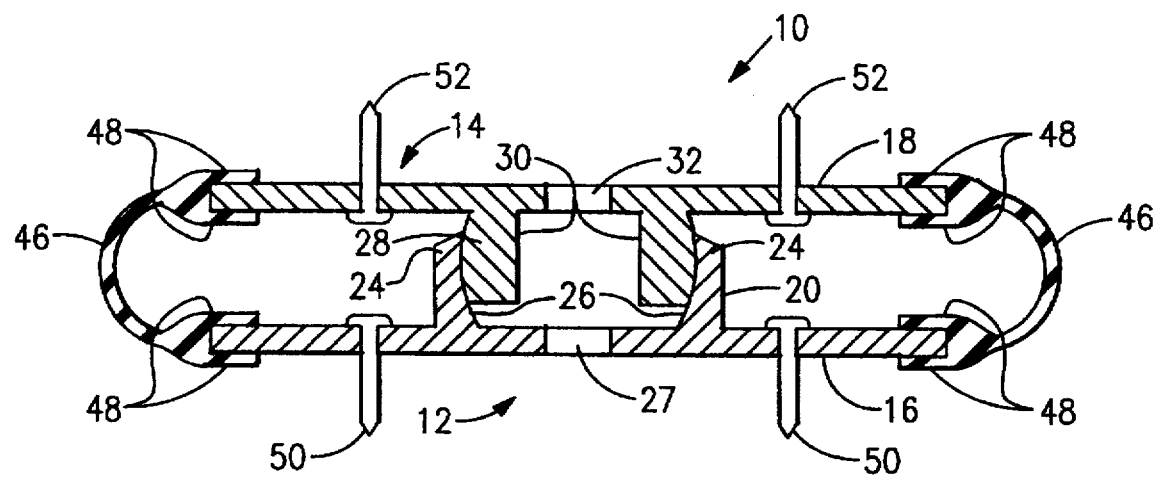
FIG. 7 is a cross sectional view taken on the line 7—7 in FIG. 1 and also showing a toroidal enclosure absent FIG. 1.

Referring momentarily to FIG. 7 in conjunction with FIG. 2, the socket 20 includes a beveled edge 24 extending along the perimeter of the second socket end 20b. The height of the socket 20 and the contour of the beveled edge 24 serve to limit the maximum amount of tilt that can be experienced by the second disk half 14 with respect to the first disk half 12 by causing the second plate 18 to contact the beveled edge 24, as is described in greater detail hereinbelow.

The inside of the socket 20 is formed into an open spherical portion 26. The spherical portion 26 is formed so as to be spherical in shape, however only a portion of an entire sphere (not shown) is included in the socket 20.

The cross sectional view of FIG. 7 reveals that the spherical portion 26 appears as a portion of the radius of the entire sphere and if a cross section were to be taken along any preferred segment of the socket, the portion of the radius of the entire sphere would appear the same as shown. Accordingly, the spherical portion 26 extends around the entire interior of the socket 20 similar to that shown in FIG. 7.

The spherical portion 26 is provided for cooperation with the second disk half 14, and is also described in greater detail hereinbelow.

A first hole 27 is provided, as desired, through the first plate 16 near the center of the socket 20.

A portion of a ball, identified in general by the reference numeral 28, is attached to the first side 18a of the second plate 18. The portion of a ball 28 is a cross sectional segment of a whole sphere (not shown).

By using the portion of a ball 28, instead of the whole sphere, the first plate 16 and the second plate 18 are adapted to be disposed in closer proximity with respect to each other, as is described in greater detail hereinbelow.

The portion of a ball 28 includes a ball radius that is slightly smaller than the radius of the spherical portion 26 so that the portion of a ball 28 is adapted to fit inside of the spherical portion 26.

If the aforementioned two radii were exactly the same size then there would be excessive friction between the outside surface of the portion of a ball 28 and the inside surface of the spherical portion 26. However the aforementioned two radii are nearly the same size so as to ensure a tight cooperative fit between the portion of a ball 28 and the spherical portion 26.

A second hole 30 is provided, if desired, through the portion of a ball 28. The second hole 30 aligns with and is adjacent to a third hole 32 that is provided, if desired, through the second plate 18 thereby providing a contiguous hole through both the portion of a ball 28 and through the the second plate 18.

The first hole 27, the second hole 30, and the third hole 32 are included as desired to aid in either the manufacture or the assembly of the first disk half 12 or to aid in either the manufacture or the assembly of the second disk half 14.

They may also be included if future testing and research indicates a need to provide a contiguous opening between a pair of adjacent vertebrae (reference numerals 34 and 36 FIG. 8). The contiguous opening is achieved by the first hole 27, the second hole 30, and the third hole 32 combined.

It is not fully understood whether a natural organic disc (reference numerals 38a, 38b, and 38c FIG. 8) provides a connective channel, such as by osmosis, between two of the adjacent vertebrae 34, 36.

However, it is the intent of the disk 10 as presently disclosed to mimic as closely as possible both the mechanical functioning and the various physiological attributes of the natural organic disc 38a, 38b, and 38c that it is intended to replace.

Further research may indeed reveal other modifications which can be made to the disk 10 in order to yield a better duplication of the function and the physiology of the natural organic disc 38a, 38b, and 38c.

Therefore the present disk 10 discloses a structure that is adapted to provide an opening from one of the pair of vertebrae 34 to an adjacent one of the pair of vertebrae 36 when the disk 10 is intermediately disposed between the pair of vertebrae 34, 36.

Numerous potential benefits and options are provided by the structure of the disk 10 in that if any type of an insert 40 (FIG. 4) may be placed where desired in any of either the first hole 27, the second hole 30, or the third hole 32. The insert 40, as shown includes a wafer shape thereto that corresponds approximately to the diameter to either the first hole 27, the second hole 30, or the third hole 32.

The insert 40 serves as either a membrane, a filter, a substance, or a barrier. The insert 40 is incorporated into the disk 10 if by either research or by other testing and trials it is revealed to be desirable to do so.

Accordingly, the disk 10 is adapted to readily receive the insert 40. The insert 34 is placed into the second hole 30 and is retained by either the friction arising from a "press-fit" or it is secured in place by a biologically tolerable adhesive.

Figure 4:
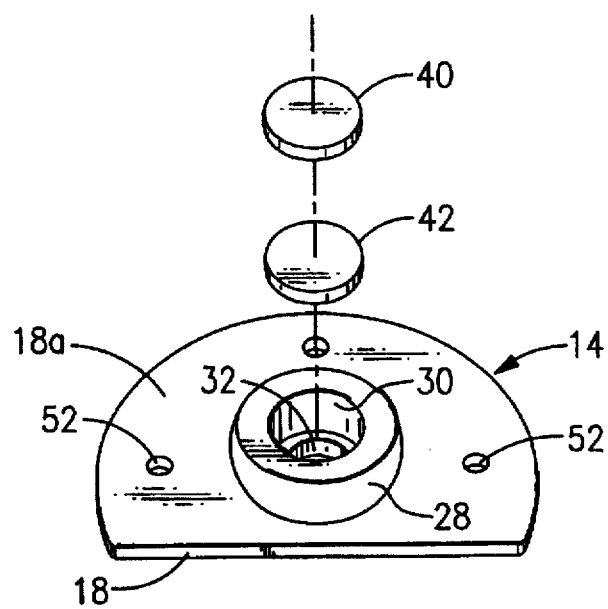
FIG. 4 is a view in perspective of a second disk half that is adapted for cooperation with the first disk half.
Figure 6:
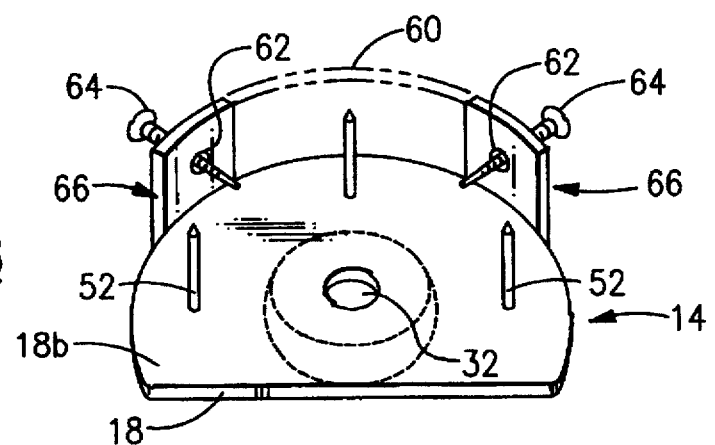
FIG. 6 is a view in perspective of the opposite side of the second disk half as shown in FIG. 4 and also showing a plurality of tabs attached thereto.

Referring now momentarily to FIGS. 1, 4, and 6, it is shown that the second hole 30 in the portion of a ball 28 is of a larger diameter than is the third hole 32 in the second plate 18. Therefore when the insert 40 is pressed down into the second hole 30 in the portion of a ball it cannot be pressed down beyond the third hole 32 having a smaller diameter in the second plate 18, which therefore serves as a mechanical stop for the insert 40.

Of course any type of adhesive, as mentioned hereinabove, can also be used to secure the insert in position, where desired providing that it is well tolerated by the human body.

It is mentioned at this time that as a related benefit, while the disk 10 is primarily intended for human use, in special circumstances the disk 10 can be varied in size to fit between two animal vertebrae (not shown) as well. The use of the disk 10 in animals is desirable as part of any potential trial to determine efficacy of the disk 10 for human use, and also the disk 10 may be useful to eliminate the physical suffering of animals.

It has been described how the insert 40 can be readily placed and secured in the second hole 30. Of course, the insert 40 can be varied in size to fit within either the first hole 27 or the third hole 32.

A second insert 42 or even further additional inserts (not shown) can also be placed in either the first hole 27, the second hole 30, or the third hole 32.

The second insert 42 is similar to the insert 40 described hereinabove in that the second insert 42 can function as either a membrane, a filter, a substance, or a barrier.

As was described in brief hereinabove, the disk 10 in intended to mimic any of the natural organic discs 38a, 38b, and 38c that it is intended to replace, in the event that replacement of them becomes necessary or desirable.

But the disk 10, no matter how well it is designed, is a foreign object that is to be inserted into the human body. Accordingly, its effect upon the body must be considered including that upon the immune system. The use of drugs which will aid the healing process, or which will make the human body more likely to accept, and therefore less likely to reject the disk 10 may be helpful.

It may be revealed that placing certain of these drugs in close proximity to the pair of vertebrae 34, 36 between which the disk 10 is to be placed, is advantageous. Accordingly the insert 40 and the the second insert 42 as shown may be formed of any substance desired including any desired drug.

For example, either the insert 40 or the second insert 42 may include a soluble drug that is absorbed by the human body to lessen the chances of rejection of the disk 10 or which may promote healing, or lessen the chances of infection by functioning as an antibiotic.

Similarly, the insert 40 may address some of these uses whilst the second insert 42 addresses other of these uses. Accordingly, the disk 10 provides both functional [mechanical] advantages as well as potential medical [therapeutic] benefits that either render the disk 10 less likely to be rejected by the immune system or which promote healing after insertion of the disk 10 has occurred and therefore serve to increase its overall biological compatibility.

As shown in FIG. 4, the second insert 42 is placed into the second hole 30 first and then the insert 40 is placed on top of the second insert 42. If the second insert 42 were to function as a soluble drug and the insert 40 were to function as a barrier, then the timed release of the soluble drug could be varied (moderated) by merely controlling the diameter of the third hole 32. If the diameter of the third hole were enlarged, the soluble drug of the second insert 42 would be dissolved sooner than if the third hole 32 were of a decreased diameter.

Referring again on occasion to all of the FIG. drawings, the first disk half 12 and the second disk half 14 are assembled together by a sufficient force to each to urge them together so that the portion of a ball 28 first aligns with and begins to enter into the socket 20 at the second socket end 20b.

As a greater force is applied thereto, the expansion slots 22 begin to expand a sufficient amount to allow the increasing diameter of the portion of a ball 28 to continue to enter further into the socket 20. As the portion of a ball 28 enters into the socket 20, eventually the diameter of the portion of a ball 28 stops increasing and begins to decrease.

At this time the portion of a ball 28 slips easily into the socket 20 until the portion of a ball 28 corresponds exactly to the shape of the socket 20. The socket 20 then resists any further entry by the portion of a ball 28 therein.

Accordingly an easy method for the assembly of the first disk half 12 and the second disk half 14 together to form the disk 10 is described.

Once the first disk half 12 is thus assembled together with respect to the second disk half 14, the portion of a ball 28 cooperates with the spherical portion 26 to mimic a range of motion comparable with a normal spine (not shown).

An especially valuable advantage the disk 10 provides arises from the use of the portion of a ball 28 and the spherical portion 26. Referring momentarily to FIG. 7, it is evident that if an entire ball (not shown) having a radius similar to that of the portion of a ball 28 were to be placed in an entire sphere (not shown) having a radius similar to that of the spherical portion 26, the size of the entire ball and the entire sphere would, of necessity, extend the first disk half 12 a greater distance apart from the second disk half 14 than is presently provided.

Observation of FIG. 7 reveals that if the portion of a ball 28 were replaced by the entire ball, then a portion of the entire ball would contact the first side 16a of the first plate 16 inside of the socket 20. The spherical portion 26 of the socket 20 would then have to be increased in size to accommodate the entire ball by an amount that would make the spherical portion 26 of socket the size of the entire sphere. Clearly this would dispose the first plate 16 and the second plate 18 further apart and therefore would also dispose the first disk half 12 a greater distance apart from the second disk half 14.

It has been shown how the use of the spherical portion 26 in cooperation with the portion of a ball 28 allows for the first disk half 12 to be disposed in closer proximity to the second disk half 14 than could be attained with the use of an entire ball and an entire sphere. There are many benefits which arise from this geometry.

First because the pair of vertebrae 34 are thus disposed closer with respect to each other there are less mechanical stresses induced upon the disk 10 when the spinal column is tilted in any direction such as by bending of the user (not shown). The further the pair of vertebrae 34 are disposed apart from each other, the greater is the moment arm that develops between them, and accordingly, the greater is the force (leverage) that is generated by the user when bending in any direction.

This phenomenon is well understood by patients whom have had spinal fusion occur whereby at least two adjacent vertebrae (not shown) are fused together to form a contiguous vertebrae (not shown). Such patients frequently experience increased stress and subsequently faster wear and degradation of those vertebrae that are adjacent to the fused vertebrae. This arises from the increased leverage that is developed from the increased moment arm (when bending) by the user. If the pair of vertebrae 34 were extended further apart by a modified prosthesis (not shown), they too would experience greater stress, wear, and eventual degradation arising from increased mechanical stresses.

Also one of the natural organic disks 38c (Refer momentarily to FIG. 8) disposes a second pair of vertebrae 44a, 44b relatively close with respect to each other. Accordingly, the disk 10 allows for the pair of vertebrae 34, 36 to be disposed apart from each other a distance that approximates that of the natural biological disk (not shown) which it replaces.

As the disk 10 allows for the pair of vertebrae 34, 36 to be extended a normal distance apart from each other, all supporting ligaments, muscles, and nerve tissues are also normally disposed and are not unduly stressed.

Another significant benefit provided by the disk 10 is that the use of the portion of a ball 28 and the spherical portion 26 provides for a range of motion about a point as is characteristic of a ball and socket type of joint while not requiring the size of an entire ball disposed within an entire socket (not shown). This provides the disk 10 with the least thickness that is possible whilst still preserving the desired range of motion.

Once assembled together the first disk half 12 and the second disk half 14 are able to experience, within limits, the motion typical of a ball and socket joint. As described hereinabove, the height of the socket 20 and the contour of the beveled edge 24 limit the maximum amount of tilt that is possible between the first disk half 12 and the second disk half 14.

A reasonable range of motion would allow about thirteen (13) degrees of tilt in any direction between the first disk half 12 and the second disk half 14 with respect to a longitudinal axis passing through the center of the disk 10 including the first hole 27, the second hole 30, and the third hole 32, when the deviation is measured from a parallel planar position between the first disk half 12 and the second disk half 14. An excessive amount of tilt would produce an excessive amount of strain that is then in turn experienced by the pair of vertebrae 34, 36. The tilt allowed may be varied from disk 10 to disk 10 to accommodate the special requirements of certain patients.

Referring now primarily to FIG. 7 is shown in cross section a flexible toroidal enclosure 46 that is shown disposed around the perimeter of the disk 10. The flexible toroidal enclosure 46 is not shown in FIG. 1 where the cross sectional view is originally taken. However it is added to the cross sectional view of FIG. 7 as this particular view readily reveals its structure and its attachment to the disk 10.

The flexible toroidal enclosure 46 is shaped like a toroid (not shown) but it is not contiguous on the inside. Therefore it closely resembles an object having the shape of the outer half of the toroid such as an automobile tire (not shown). The flexible toroidal enclosure 46 is attached to the perimeter of the first plate 16 and to the perimeter of the second plate 18.

As shown the flexible toroidal enclosure 46 includes an overlapping portion 48 which encloses the perimeter of the first plate 16 and the perimeter of the second plate 18. The overlapping portion 48 is secured to the first plate 16 and to the second plate 18 by molding it in place or by the use of an appropriate adhesive.

The flexible toroidal enclosure 46 is formed of any desired flexible elastomeric material such as rubber, silicone rubber, or similar material. Whatever material is used to form the flexible toroidal enclosure 46 it must be durable and flexible and should ideally be biologically compatible with the recipient (not shown).

The flexible toroidal enclosure 46 is included when it is desired to prevent scar tissue (not shown) from forming inside of the disk 10 during healing and when it is desired to prevent organic matter from entering into the disk 10.

Referring now to all of the FIG. drawings on occasion, the disk 10 is retained in position by any combination of any of the methods as is described in greater detail hereinafter. A plurality of first pins 50 are attached to the first plate 16 and extend from the second side 16b thereof. The first pins 50 are adapted to enter into first pin holes (not shown) that are provided in the pair of vertebrae 34, 36.

A plurality of second pins 52 are attached to the second plate 18 and extend from the second side 18b thereof. The second pins 52 are also adapted to enter into second pin holes (not shown) that are provided in the pair of vertebrae 34, 36.

Figure 5:
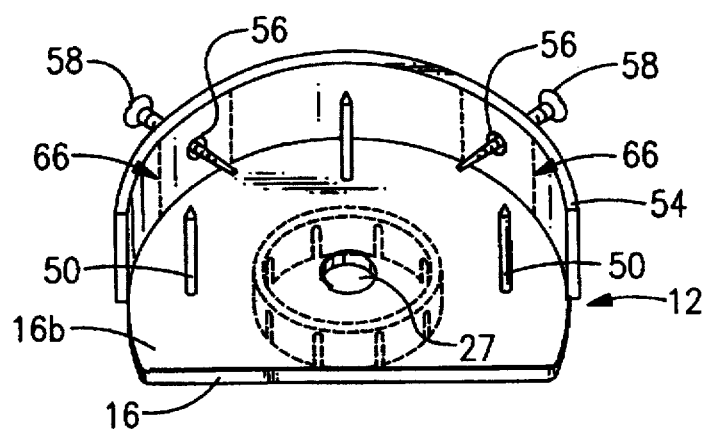
FIG. 5 is a view in perspective of the opposite side of the first disk half as shown in FIG. 3 and also showing an annulus attached thereto.

Referring momentarily in particular to FIG. 5 and to FIG. 8, a first annulus 54 is attached to the first plate 16 and extends from the second side 16b thereof. A pair of first annulus holes 56 are provided through the first annulus 54 and are adapted to receive a pair of first screws 58 which, in turn, fasten the disk 10 to the pair of vertebrae 34, 36.

The first annulus 54 surrounds a portion of one of the pair of vertebrae 36. In the event of an impact applied to the disk 10 it is important that the disk 10 resist being dislodged. The use of the first annulus 54 provides a mechanically stable approach to securing the disk 10 in position.

Referring momentarily also to FIG. 6, a second annulus 60 (shown partially in dashed lines and partially in solid lines) is attached to the second plate 18 and extends from the second side 18b thereof. A pair of second annulus holes 62 are provided through the second annulus 60 and are adapted to receive a pair of second screws 64 which, in turn, fasten the disk 10 to the pair of vertebrae 34, 36.

The second annulus 60 surrounds a portion of another of one of the pair of vertebrae 34. In the event of an impact applied to the disk 10 it is important that the disk 10 resist being dislodged. The use of the second annulus 60 provides a mechanically stable approach to securing the disk 10 in position.

If preferred, a plurality of tabs, identified in general by the reference numeral 66, may be used to secure the disk 10 in position. The tabs 66 are similar to either the first annulus 54 or to the second annulus 60 except they do not extend as far. The tabs 66 are useful when, for any reason including disease, the pair of vertebrae 34, 36 prevent the use of either the first annulus 54 or the second annulus 60. The tabs 66, which comprise a portion only of the first annulus 54 and a portion only of the second annulus 60, are shown in dashed lines in FIG. 5 and in solid lines in FIG. 6.

The invention has been shown, described and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. An artificial intervertebral disk prosthesis, comprising:
   (a) a first disk half assembly, said first disk half assembly including a first disk plate having a first side and a second side and having a substantially "D-shaped" contour thereof, and including a socket having a first socket end and an opposite second socket end, said first socket end is attached to said first side of said first disk plate;
   (b) a second disk half assembly, said second disk half assembly including a second disk plate having a first side and a second side, said second disk plate having a contour substantially the same as said first disk plate, and including a portion of a ball having a first ball portion end and an opposite second ball portion end, said first ball portion end is attached to said first side of said second disk plate, said portion of a ball configured for cooperation with said socket;
   (c) means for inserting and for retaining said portion of a ball in said socket, said means for inserting and for retaining is attached to said first disk half assembly, said means for retaining providing a sufficient resistance to an applied force to prevent separation of said first disk half assembly from said second disk half assembly;
   (d) means for retaining said disk prosthesis in a position of cooperation with at least one vertebra, said means for retaining is attached to said second side of at least one of said first and second disk plates; and
   (e) means for receiving at least one bioabsorbable insert, said means for receiving is formed in any of said first and second disk plates and said portion of ball.

2. The disk of claim 1 wherein said means for inserting and for retaining said ball into said socket includes a plurality of expansion slots found in said socket at said second socket end and extending a predetermined distance toward said first socket end.

3. The disk of claim 1 including means attached to said first side of said first disk plate for limiting the amount of tilt of said first disk half assembly with respect to said second disk half assembly.

4. The disk of claim 3 wherein said means for limiting tilt includes extending said socket second end a predetermined distance from said first side of said first plate sufficient to impinge upon a portion of said second disk plate when said first disk half assembly is tilted with respect to said second disk half assembly.

5. The disk of claim 3 wherein said means for limiting tilt includes providing a beveled edge on said socket second end.

6. The disk of claim 1 including means attached to said first disk plate and said second disk plate for enclosing said disk prosthesis.

7. The disk of claim 6 wherein said means for enclosing includes a flexible substantially toroidal shaped enclosure that is disposed around a perimeter of said first disk plate and is attached to said first disk plate and is disposed around a perimeter of said second disk plate and is attached to said second disk plate.

8. The disk of claim 1 wherein said means for retaining said disk prosthesis in a position of cooperation includes means for attaching said disk to said at least one vertebra.

9. The disk of claim 8 wherein said means for attaching includes at least one protrusion attached to said first disk plate and extending from said second side of said first disk plate, said at least one protrusion adapted for cooperation with said at least one vertebra.

10. The disk of claim 8 wherein said means for attaching includes at least one protrusion attached to said second disk plate and extending from said second side of said second disk plate, said at least one protrusion adapted for cooperation with said at least one vertebra.

11. The disk of claim 8 wherein said means for attaching includes at least one tab attached to said first disk plate and extending from said second side of said first disk plate, said at least one tab including at least one hole therein.

12. The disk of claim 8 wherein said means for attaching includes at least one tab attached to said second disk plate and extending from said second side of said second disk plate, said at least one tab including at least one hole therein.

13. The disk of claim 8 wherein said means for attaching includes an annular ring attached to said first disk plate, said annular ring extending away from said second side of said first disk plate and including at least one hole therein.

14. The disk of claim 8 wherein said means for attaching includes an annular ring attached to said second disk plate, said annular ring extending away from said second side of said second disk plate and including at least one hole therein.

15. The disk of claim 1 wherein said disk includes a second bioabsorbable insert that forms a filter.

16. The disk of claim 1 wherein said disk includes a second bioabsorbable insert that forms a membrane.

17. The disk of claim 1 wherein said at least one bioabsorbable insert includes a second insert that forms a barrier which affects the passage of said at least one bioabsorbable insert into a tissue of a living organism.

18. The disk of claim 1 wherein said at least one bioabsorbable insert includes a bioabsorbable substance that is dissolved over a period of time when said disk prosthesis is placed within a living organism.

19. The disk of claim 18 wherein said bioabsorbable substance is absorbed by a tissue of a living organism over a period of time when said disk prosthesis is placed within said living organism.

20. The disk of claim 1 wherein said socket defines a portion of a sphere.

21. The disk of claim 1 wherein said portion of a ball defines a portion of a sphere.

22. An artificial intervertebral disk prosthesis, comprising:
- (a) a first disk half assembly, said first disk half assembly including a first disk plate having a first side and a second side and having a substantially "D-shaped" contour thereof, and including a socket having a first socket end and an opposite second socket end, said first socket end is attached to said first side of said first disk plate;
- (b) a second disk half assembly, said second disk half assembly including a second disk plate having a first side and a second side, said second disk plate having a contour substantially the same as said first disk plate, and including a portion of a ball having a first ball portion end and an opposite second ball portion end, said first ball portion end is attached to said first side of said second disk plate, said portion of a ball configured for cooperation with said socket;
- (c) means for inserting and for retaining said portion of a ball in said socket, said means for inserting and for retaining attached to said first disk half assembly;
- (d) means for retaining said disk prosthesis in a position of cooperation with at least one vertebra, said means for retaining attached to said artificial intervertebral disk prosthesis; and
- (e) means for receiving at least one bioabsorbable insert therein, said means for receiving attached to said artificial intervertebral disk prosthesis including a first hole through said first plate, a second hole through said said socket, and a third hole through said second plate, said first hole, said second hole, and said third hole defining an opening through said disk prosthesis.

23. The disk of claim 22 wherein said bioabsorbable insert includes a substance that is therapeutically effective.

24. An artificial intervertebral disk prosthesis, comprising:
- (a) a first disk half assembly, said first disk half assembly including a first disk plate having a first side and a second side and having a substantially "D-shaped" contour thereof, and including a socket having a first socket end and an opposite second socket end, said first socket end is attached to said first side of said first disk plate;
- (b) a second disk half assembly, said second disk half assembly including a second disk plate having a first side and a second side, said second disk plate having a contour substantially the same as said first disk plate, and including a portion of a ball having a first ball portion end and an opposite second ball portion end, said first ball portion end is attached to said first side of said second disk plate, said portion of a ball configured for cooperation with said socket;
- (c) means for inserting and for retaining said portion of a ball in said socket, said means for inserting and for retaining attached to said first disk half assembly;
- (d) means for retaining said disk prosthesis in a position of cooperation with at least one vertebra, said means for retaining attached to said artificial intervertebral disk prosthesis; and
- (e) means for receiving at least one filter, said means for receiving attached to said intervertebral disk prosthesis.

* * * * *